United States Patent
Cahan et al.

(10) Patent No.: US 8,868,194 B2
(45) Date of Patent: Oct. 21, 2014

(54) AORTIC PACEMAKER

(75) Inventors: Amos Cahan, Mevaseret Zion (IL); David Planer, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 1605 days.

(21) Appl. No.: 12/295,166

(22) PCT Filed: Mar. 29, 2007

(86) PCT No.: PCT/IL2007/000420
§ 371 (c)(1),
(2), (4) Date: Sep. 29, 2008

(87) PCT Pub. No.: WO2007/113818
PCT Pub. Date: Oct. 11, 2007

(65) Prior Publication Data
US 2009/0112285 A1 Apr. 30, 2009

Related U.S. Application Data

(60) Provisional application No. 60/787,326, filed on Mar. 31, 2006.

(51) Int. Cl.
*A61N 1/00* (2006.01)
*A61N 1/365* (2006.01)
*A61N 1/36* (2006.01)

(52) U.S. Cl.
CPC ........ *A61N 1/36571* (2013.01); *A61N 1/36564* (2013.01); *A61N 1/36114* (2013.01); *A61N 1/36528* (2013.01); *A61N 1/36557* (2013.01)
USPC .......................................................... 607/48

(58) Field of Classification Search
CPC . A61N 1/36; A61N 1/36557; A61N 1/36114; A61N 1/36571; A61F 2/06; A61M 29/00; A61M 2230/08; A61M 2230/10
USPC ............................ 607/48, 119, 32, 59; 600/18
See application file for complete search history.

(56) References Cited

U.S. PATENT DOCUMENTS

| | | | | |
|---|---|---|---|---|
| 5,324,323 | A * | 6/1994 | Bui | 607/119 |
| 2002/0193841 | A1 * | 12/2002 | Betzold | 607/32 |
| 2003/0233023 | A1 * | 12/2003 | Khaghani et al. | 600/18 |
| 2008/0215117 | A1 * | 9/2008 | Gross | 607/59 |

OTHER PUBLICATIONS

International Search Report mailed Aug. 7, 2008 for PCT/IL07/00420 filed Mar. 29, 2007.
Written Opinion of the International Searching Authority mailed Aug. 7, 2008 for PCT/IL07/00420 filed Mar. 29, 2007.
International Preliminary Report on Patentability published Mar. 10, 2009 for PCT/IL2007/000420 filed Mar. 29, 2007.

* cited by examiner

*Primary Examiner* — Christopher D Koharski
*Assistant Examiner* — Roland Dinga
(74) *Attorney, Agent, or Firm* — Martin Fleit; Paul D. Bianco; Fleit Gibbons Gutman Bongini & Bianco PL (57) ABSTRACT

The present invention depicts an implantable artificial pacemaker (AAP) comprising oscillatory means providing pulsating signals at a pre-selected frequency, wherein the pacemaker is pacing the aorta. The invention also describes an AAP further comprising; (i) a plurality of sensors disposed internally or externally to the aorta; and (ii) a pacing means in which the AAP stimulates the aortic media, augmenting physiological aortic elastic recoil. An AAP further comprising a processor capable of obtaining information from sensors and triggering an appropriate contraction wave in the aortic media is also introduced. A method of managing aortic rhythm comprising; (i) implanting an AAP comprising oscillatory means; and (ii) pulsating signals at a preselected frequency, so as to pace the aorta and in which the pulsating signals are provided by synchronizing and coordinating activation impulses in a portion of the aorta using electrical impulses is also taught.

31 Claims, 11 Drawing Sheets

AORTIC PACEMAKER

FIELD OF THE INVENTION

The present invention generally relates to implantable medical devices and more specifically to devices and methods for improving cardiac function by selectively pacing the aortic media.

BACKGROUND OF THE INVENTION

The aorta is an elastic artery and as such is quite distensible, stretching and expanding when blood is forced into it from the left ventricle. This stretching creates the potential energy that helps maintain blood pressure during diastole; when the heart relaxes after contraction, the aorta contracts passively.

Myocardial perfusion is almost solely diastolic; the force that allows blood flow through the coronary arteries is dependent on the difference between the intra-aortic diastolic pressure and the left ventricular diastolic pressure. The coronary arteries originate from the aortic stem and penetrate the wall of the heart. Increased resistance to flow in the coronary arteries may be caused by atherosclerosis or increased diastolic intraventricular pressure from ischemia or cardiomyopathy, compromising coronary flow and causing myocardial ischemia.

Several clinical conditions are of relevance to the functioning of the aorta and control of blood flow during systole and diastole. Acute myocardial ischemia and other conditions cause cardiogenic shock, in which heart malfunction results in cardiac output inadequate for maintaining vital organ function. Pulmonary edema is a complication of cardiogenic shock that further impairs tissue oxygenation and may lead to death. Heart failure is also a chronic condition associated with increased morbidity and mortality and poor quality of life. In aortic regurgitation, impaired closure of the aortic valve causes retrograde blood flow from the aorta into the left ventricle during diastole, resulting in increased diastolic intra-aortic pressure, ventricular volume overload and left ventricle (LV) dilatation and eventually congestive heart failure.

Currently medical management of ischemic heart disease is primarily focused on slowing atherosclerosis, preventing thrombosis and coronary angioplasty using catheterization and coronary bypass surgery. Chronic heart failure is usually treated medically but may require heart transplantation or use of a Left or Right Ventricular Assist Device (L- or R-VAD).

Heart transplantation is problematic in that there are insufficient donors and immunosuppression is required. While LVAD can be used in the long-term it is generally used for those awaiting donor hearts and is patients are plagued by infection and require anticoagulants to prevent blood clotting caused by the blood passing over non-biological surfaces. Intra-aortic balloon pumps may be inserted in the case of acute LV failure unresponsive to treatment but this treatment is limited to a short period of time due to infection and thrombotic complication. Aortic regurgitation is treated medically by drugs that reduce the arterial resistance (afterload reduction) or by aortic valve replacement in advanced disease. Reducing LV diastolic pressure by pre- and afterload reduction by nitrates and diuretics is the mainstay of treatment in case of pulmonary edema.

Heart contractions are controlled by electrical impulses created by cardiac pacemaker cells but for many years artificial devices have been installed after damage to the body's intrinsic conduction system to produce these impulses synthetically. These existing artificial pacemakers are medical devices designed to regulate the beating of the heart itself. More recently implantable cardioverter-defibrillators (ICD) resembling cardiac pacemakers have been used in patients at risk of sudden cardiac death. ICD's have the ability to treat many types of heart rhythm disturbances by means of pacing, cardioversion or defibrillation. The device contains the rudiments of cardiac arrhythmia detection and treatment and primarily deals with ventricular fibrillation but is now also used to deal with atrial and ventricular arrhythmias. ICD implantation is similar to implantation of a cardiac pacemaker, these devices typically include a wire that runs through the right chambers of the heart and usually ends in the apex of the right ventricle. They constantly monitor the rate and rhythm of the heart and can deliver therapies when the heart rate goes over a certain number: sensors can detect rate discrimination, rhythm discrimination and morphology discrimination.

In the aortic pacemaker constant monitoring of a wide variety of parameters means that it may be activated chronically for congestive heart failure, aortic regurgitation or aortic aneurysm, or activated in a chronic-intermittent manner, for example in the case of exertional angina. The pacemaker can be used for acute incidents such as cardiogenic shock or for a limited period of time following myocardial infarction or myocarditis.

As can be seen medical and surgical treatment for heart conditions are limited and many of the surgical procedures are highly invasive and prone to infection or involve high risk surgery. While pacemakers of various types exist, these are used to regulate cardiac conduction. There is an obvious clinical benefit to globally increasing coronary blood flow, but no such treatment is available. In addition there is no treatment apart from aortic valve replacement to selectively and efficiently block blood regurgitation to the LV in aortic valve insufficiency. Thus an aortic pacemaker to selectively pace the aortic media is a long-felt need.

SUMMARY OF THE INVENTION

It is one object of the present invention to disclose an implantable artificial aortic pacemaker (AAP) that comprises an oscillatory means providing pulsating signals at a preselected frequency to the aorta, thereby pacing the aorta. It is also in the scope of the present invention to disclose an AAP further comprising of a plurality of sensors disposed internally or externally to the aorta and a pacing means wherein the AAP stimulates the aortic media, augmenting physiological aortic elastic recoil.

It is also in the scope of the present invention wherein the sensors are selected from a group consisting of chemical, mechanical or electrical sensors or any combination thereof.

It is also in the scope of the present invention to disclose a sensor wherein mechanical sensors detect parameters selected from a group consisting of aortic wall pressure, left ventricle end diastolic volume and pressure, end systolic volume and pressure, ventricular or atrial wall pressure, aortic wall potential, systolic and diastolic blood pressure or any combination thereof.

It is also in the scope of the present invention, wherein the chemical sensors detect parameters selected from a group consisting of pH in the myodcardium, lactate sensors, troponin sensors or any other chemical means to enable early detection of myodcardial ischemia.

It is also in the scope of the present invention, wherein the electrical sensors detect parameters selected from a group consisting of aortic diameter by M-mode echocardiography, aortic blood flow velocity by suing Doppler ultrasound, ECG, saturated hemoglobin fraction by using oximetry and input from any external device which is not part of the pacemaker by means of telemetry or any combination thereof.

It is also in the scope of the present invention to disclose an AAP, further comprising a processor capable of obtaining information from the sensors and triggering an appropriate contraction wave in the aortic media.

It is also in the scope of the present invention, wherein the processing means is implantable as part of the pacemaker body and/or is external, able to transmit and receive information through telemetry.

It is also in the scope of the present invention, wherein the pacing means comprises a chain of bi-polar electrodes, placed along the aorta, in location and distances according to the specific indication and hemodynamic needs.

It is also in the scope of the present invention wherein the electrodes are an adjunct to the aorta either glued to the aorta or anchored to the aorta using e.g., invasive immobilizing means.

It is also in the scope of the present invention wherein the electrode chain is formed by using discrete electrodes or at least one adapter capable of accommodating a few electrodes and connecting them to the aorta.

It is also in the scope of the present invention wherein the electrodes are connected to any location along the adapter.

It is also in the scope of the present invention wherein the said electrode anchoring means are separated by pre-determined distances on the adapter.

It is also in the scope of the present invention to disclose a pacing means capable of modifications in its pulsating intensity, velocity or direction in response to feedback from the sensing means by pre-specified algorithms.

It is also in the scope of the present invention to disclose an AAP adapted for driving blood anterogradely from the aorta to perfuse the body's end organs; retrogradely for increasing coronary artery blood flow or a combination of both; either simultaneous or sequential anterograde and retrograde contractions.

It is another object of the present invention to disclose a method of managing aortic rhythm comprising; implanting an AAP comprising oscillatory means and pulsating signals at a preselected frequency, so as to stimulate the aorta.

It is also in the scope of the present invention wherein the pulsating signals are provided by the electrodes, so as to create a synchronized and coordinated activation impulse in a portion of the aorta using electrical impulses.

It is also in the scope of the present invention to disclose a method of augmenting cardiac output comprising synchronizing the pulsating aorta such that blood is pumped anterogradely.

It is also in the scope of the present invention to disclose a method of increasing coronary perfusion comprising synchronizing the pulsating aorta such that blood is pumped retrogradely.

It is also in the scope of the present invention to disclose a method of augmenting cardiac output while increasing coronary perfusion comprising synchronizing the pulsating aorta such that pulses originate at a certain point and proceed in both retrograde and anterograde directions.

It is also in the scope of the present invention, wherein the implanting is provided by a procedure selected from a group including applying minimally invasive cervical mediastinoscopy; applying canulation of the thoracic duct, applying cardiac catheterization using arterial or venous access; or any combination thereof.

It is also in the scope of the present invention to disclose a method comprising activating contraction waves in the aortic media at a rate of 1 in every N heartbeats, where N is any integer equal to or greater than 1, but preferably N is between 1 and 6.

It is also in the scope of the present invention to disclose a method comprising self-adjusting contraction wave velocity according to aortic smooth muscle depolarization and repolarization rates so as to avoid aortic contraction during systole.

It is also in the scope of the present invention to disclose a method comprising stimulation of the contraction wave area, duration or intensity so as to promote aortic muscular layer adaptation to rhythmical contraction with decreased fatigue and improved endurance or for inducing aortic muscle hypertrophy or hyperplasia.

It is also in the scope of the present invention to disclose a method of inducing smooth muscle proliferation and improving performance over time comprising implanting an AAP comprising oscillatory means; pulsating signals at a preselected frequency, hence stimulating the aorta.

It is also in the scope of the present invention to disclose a method especially adapted for treating acute cardiac insult selected from a group including cardiogenic shock; myocardial infarction or myocarditis, comprising the steps of implanting an AAP following the insult or activating pre-implanted AAP, and pulsating signals at a preselected frequency, hence stimulating the aorta.

It is also in the scope of the present invention to disclose a method especially adapted for treating medical conditions selected from a group including congestive heart failure, pulmonary edema, aortic regurgitation and aortic aneurysm comprising the steps of implanting an AAP, continuously pulsating signals at a preselected frequency, hence stimulating the aorta and restoring and maintaining cardiovascular equilibrium.

It is also in the scope of the present invention to disclose a method especially adapted for treating exertional angina, comprising the steps of implanting an AAP, triggering AAP activation in times of need, pulsating signals at a preselected frequency, hence stimulating the aorta.

It is also in the scope of the present invention wherein the triggering of the AAP is provided by means selected from a group including, sensors, manual activation by a patient or medical caregiver, or from a remote site especially an emergency hot line, or any combination thereof.

It is also in the scope of the present invention wherein said pulsating is activated by a group of triggers including intrinsic cardiac activity, artificial cardiac pacemaker or hemodynamics sensed by the aortic electrodes.

BRIEF DESCRIPTION OF THE FIGURES

The objects and advantages of various embodiments of the invention will become apparent from the following description when read in conjunction with the accompanying drawings wherein;

FIGS. 4A-4B illustrate the layers of the aortic wall, wherein FIG. 4A shows a photographic image of the layers of the aortic wall (40a) and FIG. 4B represents the aortic walls (40b);

FIGS. 5A-5B schematically represent the contraction wave, wherein

DETAILED DESCRIPTION OF THE EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art since the generic principles have been defined especially to provide means and methods of providing a portable and implantable device for selective pacing of the aortic media. The present invention overcomes the disadvantages of the prior art by providing novel devices and a method for activating the aortic media of patients suffering from heart or circulatory diseases. The device is specifically designed to pulsate locations in the aorta The term 'aorta' refers hereinafter in a non-limiting manner to at least one location within or on top of the said aorta, and in which the aorta is the artery originating from the left ventricle of the heart and running in the thorax and abdomen, bringing oxygenated blood to all parts of the body in the systemic circulation.

The term 'aortic media' refers hereinafter in a non-limiting manner to the muscular layers of the aorta.

The term 'pulsating' refers hereinafter in a non-limiting manner to rhythmic expansion and contraction of the aorta and the aortic media.

The term 'stimulating' refers hereinafter in a non-limiting manner to enhancement of aortic activity either independently or synchronized with the heart during either systole or diastole.

The term 'equilibrium' refers hereinafter in a non-limiting manner to the condition of the body in which competing influences are balanced.

The term 'pacemaker body' refers hereinafter in a non-limiting manner to a unit of the artificial aortic pacemaker containing the battery, pulse generator and control unit of the device.

It is one embodiment of the present invention to provide an implantable artificial aortic pacemaker (AAP) comprising oscillatory means providing pulsating signals at a pre-selected frequency. According to another embodiment of the present invention, the AAP is further comprising a plurality of sensors disposed internally or externally to the aorta and a pacing means; such that the AAP stimulates the aortic media, augmenting physiological aortic elastic recoil.

It is yet another embodiment of the present invention wherein the sensors may be selected from a group consisting of chemical, mechanical or electrical sensors or any combination thereof. In this embodiment, the mechanical sensors detect parameters selected from a group consisting of aortic wall pressure, left ventricle end diastolic volume and pressure, end systolic volume and pressure, ventricular or atrial wall pressure, aortic wall potential, systolic and diastolic blood pressure or any combination thereof. Also according to this embodiment chemical sensors detect parameters selected from a group consisting of pH in the myodcardium, lactate sensors, troponin sensor or any other chemical means to enable early detection of myodcardial ischemia. Additionally electrical sensors detect parameters selected from a group consisting of aortic diameter by M-mode echocardiography, aortic blood flow velocity by suing Doppler ultrasound, ECG, saturated hemoglobin fraction by using oximetry and input from any external device which is not part of the pacemaker by means of telemetry or any combination thereof.

According to another embodiment of the present invention the AAP may further comprise a processor or control unit capable of obtaining information from said sensors and triggering an appropriate contraction wave in the aortic media. In this embodiment, the processing means is implantable as part of the pacemaker body and/or is external, able to transmit and receive information through telemetry.

In yet another embodiment of the present invention, the pacing means comprises a chain of bi-polar electrodes, placed along the aorta, in location and distances according to the specific indication and hemodynamic needs. According to this embodiment the electrodes are adjunct to the aorta either glued to the aorta or anchored to the aorta using for example, invasive immobilizing means. Additionally the electrode chain may be formed by using discrete electrodes or at least one adapter capable of accommodating a few electrodes and connecting them to the aorta. Also according to this embodiment, the electrodes are connected to any location along the adapter and the electrode anchoring means are separated by pre-determined distances.

According to another embodiment of the present invention, the pacing means is capable of modifications in its pulsating intensity, velocity or direction in response to feedback from the sensing means by pre-specified algorithms.

In yet another embodiment of the present invention, the AAP is adapted for driving blood anterogradely from the aorta to perfuse the body's end organs; retrogradely for increasing coronary artery blood flow or a combination of both; either simultaneous or sequential anterograde and retrograde contractions.

According to another embodiment of the present invention, a method of managing aortic rhythm is introduced, comprising implanting an AAP comprising oscillatory means and pulsating signals at a preselected frequency, so as to stimulate the aorta. The pulsating signals are provided by electrodes, so as to create a synchronized and coordinated activation impulse in a portion of the aorta using electrical impulses. A method of augmenting cardiac output comprising synchronizing the pulsating aorta such that blood is pumped anterogradely is yet another embodiment of the present invention. According to another embodiment of the present invention a method of increasing coronary perfusion comprising synchronizing the pulsating aorta such that blood is pumped retrogradely is disclosed. A method of augmenting cardiac output while increasing coronary perfusion comprising synchronizing said pulsating aorta such that pulses originate in a certain point and proceed in both retrograde and anterograde directions is another embodiment of the present invention.

In yet another embodiment of the present invention, implanting of the AAP is provided by a procedure selected from a group including applying minimally invasive cervical mediastinoscopy; applying canulation of the thoracic duct, applying cardiac catheterization using arterial or venous access; or any combination thereof. In another embodiment of the present invention, a method of implanting the AAP is provided by open surgery or laparoscopy.

According to another embodiment of the present invention a method comprising activating contraction waves in the aortic media at a rate of 1 in every N heartbeats, where N is any integer equal to or greater than 1, but preferably N is between 1 and 6, is disclosed.

In yet another embodiment of the present invention, a method, comprising self-adjusting contraction wave velocity according to aortic smooth muscle depolarization and repolarization rates so as to avoid aortic contraction during systole is disclosed.

A method comprising stimulating of the contraction wave area, duration or intensity so as to promote aortic muscular layer adaptation to rhythmical contraction or for inducing aortic muscle hypertrophy or hyperplasia is another embodiment of the present invention.

According to another embodiment of the present invention the method especially adapted for inducing smooth muscle proliferation and improving aortic contraction performance over time comprises implanting an AAP comprising oscillatory means; pulsating signals at a preselected frequency, hence stimulating the aorta is disclosed.

The method especially adapted for treating acute cardiac insults selected from a group including cardiogenic shock; myocardial infarction or myocarditis, comprises the steps of implanting an AAP following said insult, pulsating signals at a preselected frequency, hence stimulating the aorta is yet another embodiment of the present invention.

The method especially adapted for treating medical conditions selected from a group including congestive heart failure, pulmonary edema, aortic regurgitation and aortic aneurysm comprising the steps of implanting an AAP, continuously pulsating signals at a preselected frequency, hence stimulating the aorta and maintaining cardiovascular equilibrium is also an embodiment of the present invention.

The method especially adapted for treating exertional angina or angina equivalent, comprising the steps of implanting an AAP, triggering AAP activation in times of need, pulsating signals at a preselected frequency, hence stimulating the aorta is yet another embodiment of the present invention. According to this embodiment, said triggering is provided by a means selected from a group including, sensors, manual activation by a patient or medical caregiver, or from a remote site especially an emergency hot line, or any combination thereof. A method wherein said pulsating is activated by a group of triggers including intrinsic cardiac activity, artificial cardiac pacemaker or hemodynamics sensed by the aortic electrodes is yet another embodiment of the present invention.

Figure 1:
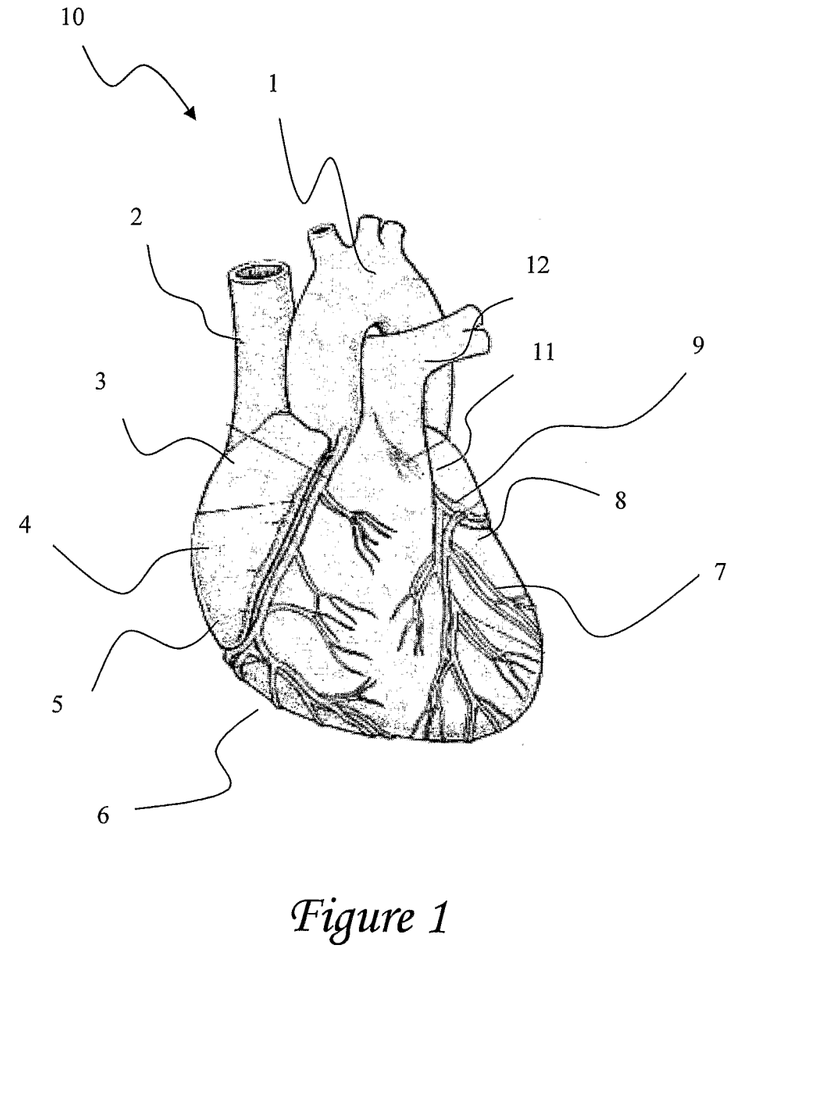
FIG. 1 illustrates the main structures of the human heart.
Figure 2:
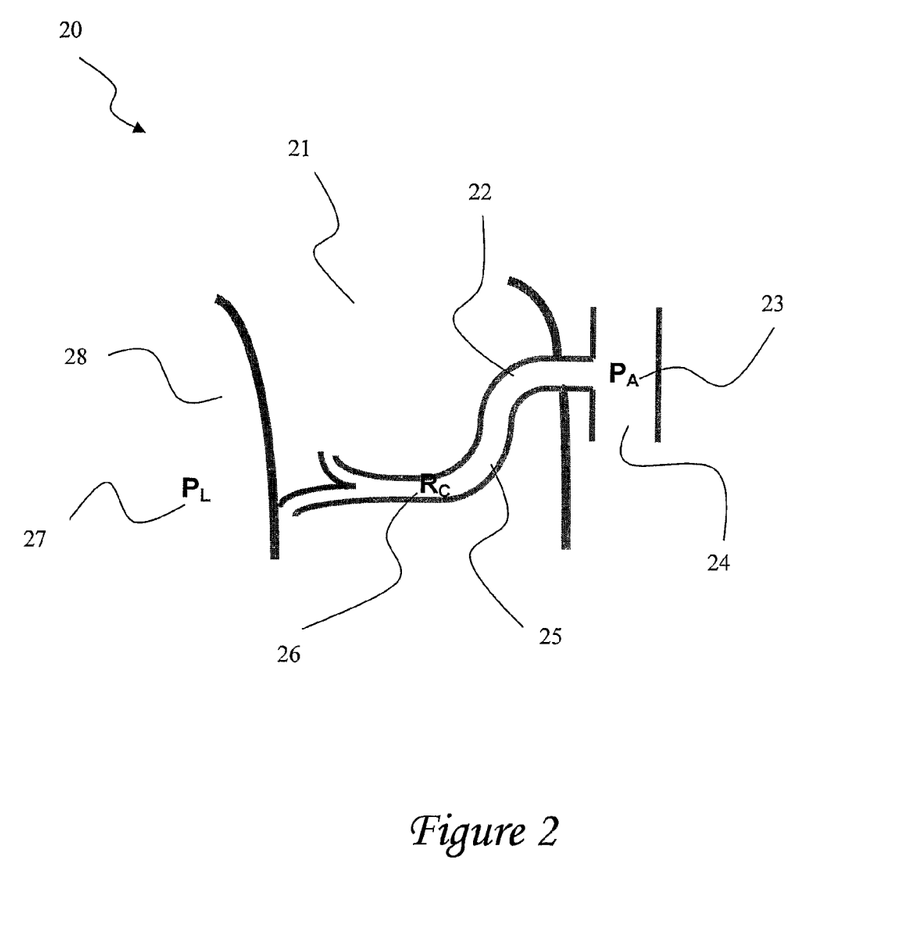
FIG. 2 schematically represents coronary perfusion to the heart.

Reference is now made to FIGS. 1, 2, 3 and 4 in the prior art showing the structure and function of the heart. FIG. 1 illustrates a human heart (10) and its component parts including the ascending aortic arch (1), superior vena cava (2), right coronary artery (3), anterior cardiac vein (4), right atrium (5), right ventricle (6), left ventricle (7), great coronary vein (8), left atrium (9), right coronary artery (11) and the pulmonary artery. FIG. 2 schematically represents the mechanics of coronary perfusion (20), in which the penetrating branch (25) of the coronary artery (22), exits the aorta (24) and enters the ventricular wall (21), approaching the ventricular lumen (28). $P_A$ (23) represents the arterial diastolic pressure, $R_C$ (26) represents the resistance of coronary arteries and $P_L$ (27) represents luminal (ventricular lumen) diastolic pressure. The forces experienced in these blood vessels can be described by the following equations;

$I_C = V/R$, such that $V = P_A - P_L$ and $R_C \propto 1/r^4$ and in which $I_C$ is coronary perfusion or current, V is the potential energy and R is the resistance, according to Ohm's Law. $R_C$ is the resistance of the coronary arteries and r is the radius of the artery, such that if you decrease the radius of an artery by 50%, for example in an atherosclerotic arteries, then resistance will increase by a factor of 16.

Figure 3A:
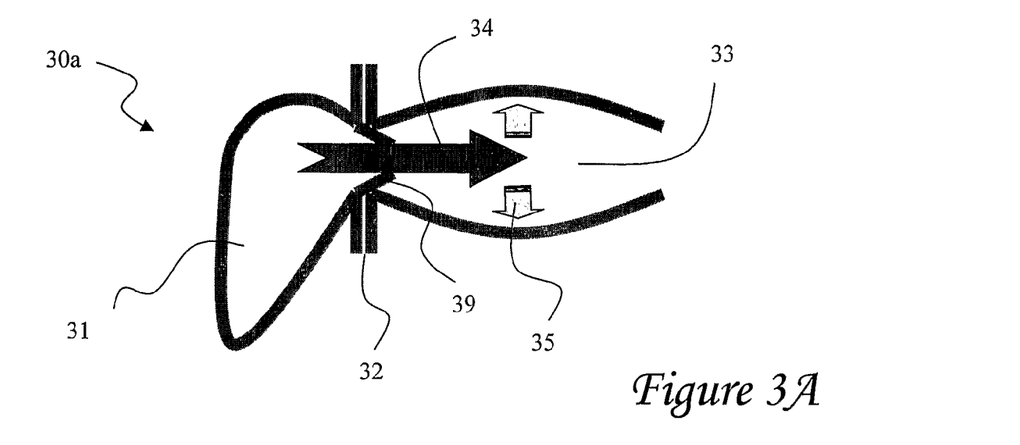
FIGS. 3A-3B schematically represent blood flow during systole (3A) and diastole (3B)
Figure 3B:
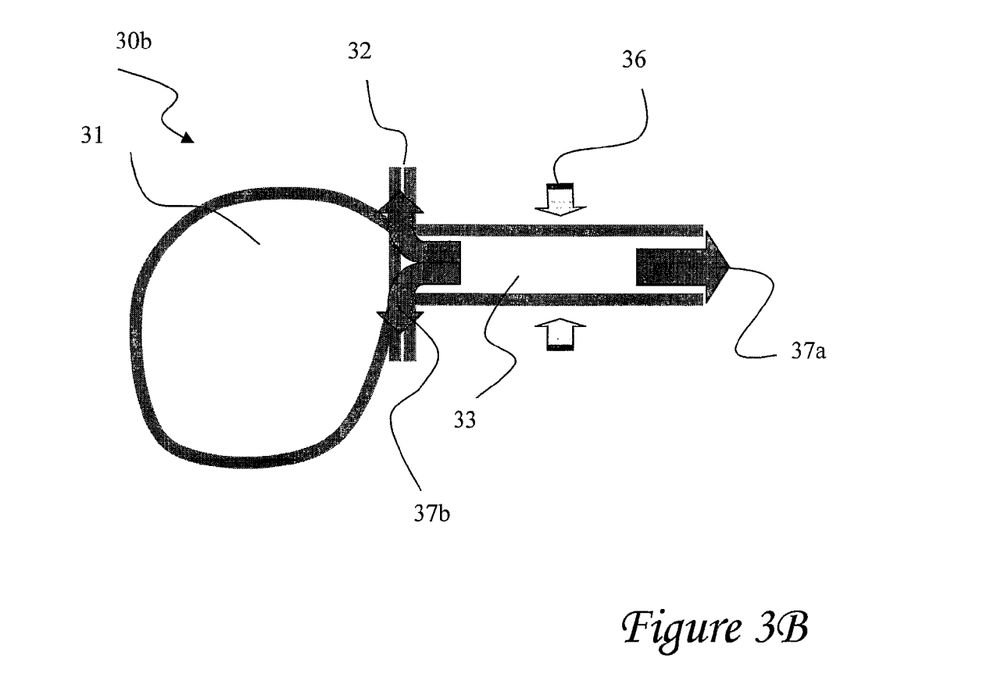

FIG. 3A schematically illustrates the forces involved in aortic pulsation during systole (30a). The left ventricle (31) contracts, pushing open the aortic valves (39) and forcing blood (34) directly into the aorta (33), without entering the coronary arteries (32) to perfuse the end organs of the body. The force of the blood entering the aorta stretches the walls of the aorta (38), creating the potential energy that helps maintain blood pressure during diastole. FIG. 3B shows the forces involved in aortic pulsation during aortic diastole (30b). When the heart relaxes after contraction, the aorta (33) contracts passively (36) as the aortic walls (38) relax, the aortic valves (39) close and blood is either pushed forward (37a) to perfuse the end organs of the body or backwards (37b) to perfuse the coronary arteries, or in both direction to improve coronary flow while increasing cardiac output.

Figure 4A:
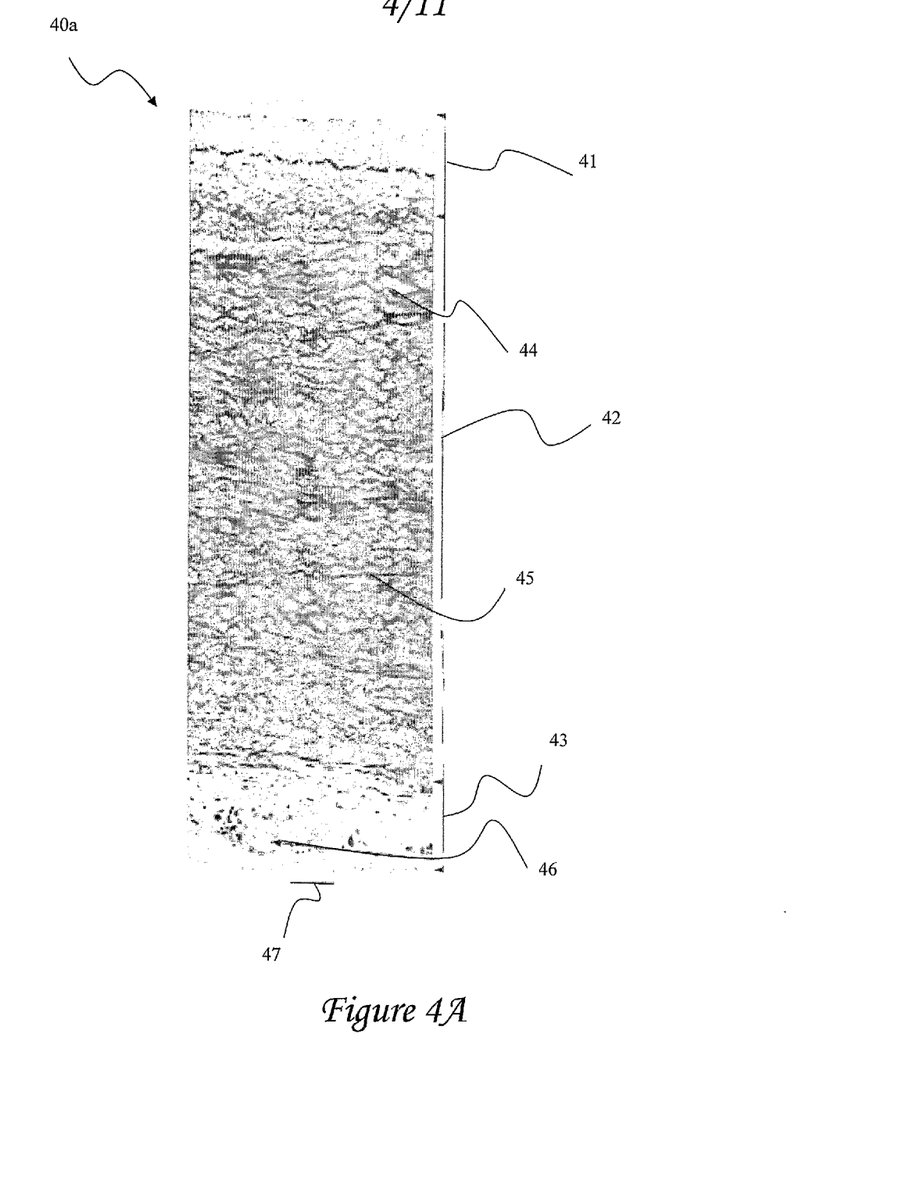
Figure 4B:
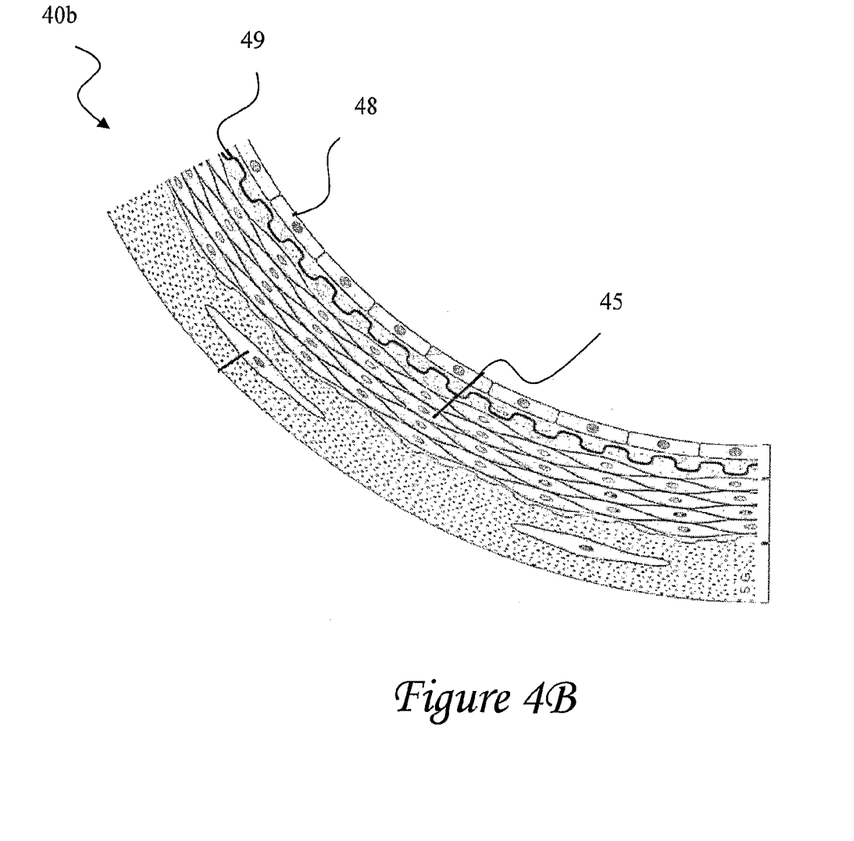

Reference is now made to FIG. 4, showing the aortic wall. In FIG. 4A a photographic image of the layers of the aortic wall (40a) is shown. The tunica intima (41) is the innermost layer of the aortic wall. The next layer is the tunica media (42), made of smooth muscle cells (45) and a considerable quantity of elastic fibres (44). The outermost layer is known as the tunica adventitia (43) and is also known as the tunica externa and is made up mostly of collagen to help anchor the aorta in its surrounding tissue. Most cells, including those of the aorta, need to be within a few cell-widths of a capillary to stay alive, the network of smaller vessels that supply these cells is known as the vasa vasorum (46). The vasa vasorum penetrates the tunica adventitia, as well as the deeper tunica media of large vessels such as the aorta. The scale bar (47) in this image represents 100 μM. FIG. 4B schematically represents the aortic walls (40b), in this figure the layers of the aorta, the tunica intima (41), tunica media (42) and the tunica adventitia (43) are shown. It can be seen that the tunica intima is made up of one layer of endothelial cells (48), supported by an internal elastic lamina (49). The endothelial cells are in direct contact with the blood flow in the lumen (401) of the aorta. The smooth muscle cells (45) of the tunica media are also shown. The tunica adventitia additionally contains fibroblasts (402).

Figure 5A:
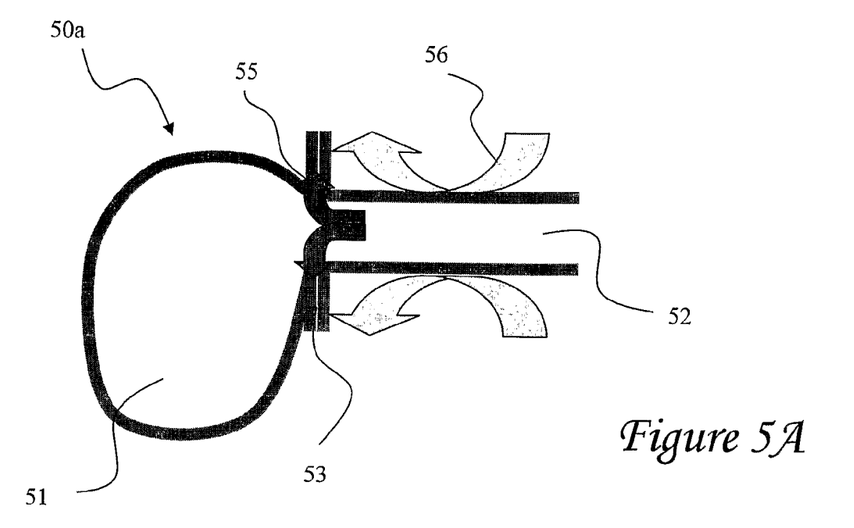
FIG. 5A shows increased coronary perfusion (50b) and FIG. 5B shows increased cardiac output (50b)
Figure 5B:
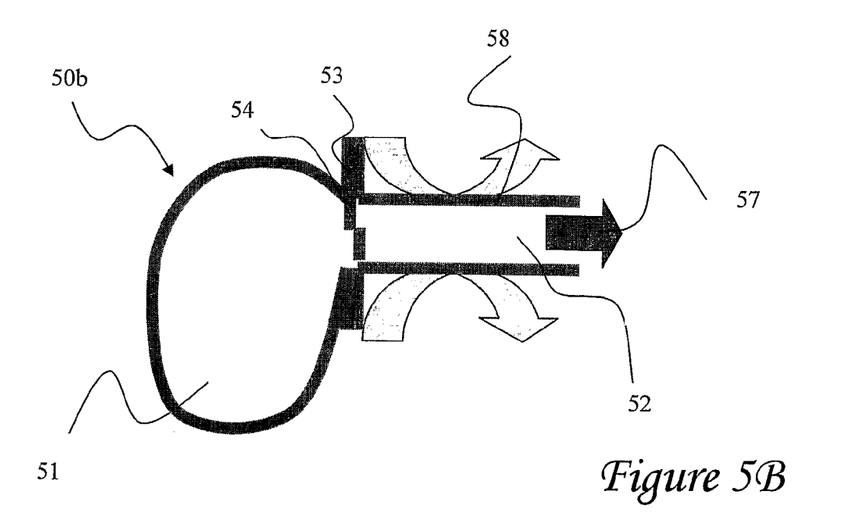

Reference is now made to FIG. 5 in which the different directions of active aortic contraction are shown. FIG. 5A schematically represents how coronary perfusion (50b) may be increased. The electrodes of the aortic pacemaker activate a retrograde contraction wave (56) in the aorta (52), pushing blood (55) in the direction of the coronary arteries (53), but not into the left ventricle (51). In FIG. 5B, increased cardiac output (50b) is schematically illustrated. The aortic valves (54) are closed such that blood does not enter the left ventricle. The anterograde contraction wave (58) activated by the aortic pacemaker, pushes the blood (57) forward, thereby increasing cardiac output and improving perfusion of the body's end organs.

Figure 6:
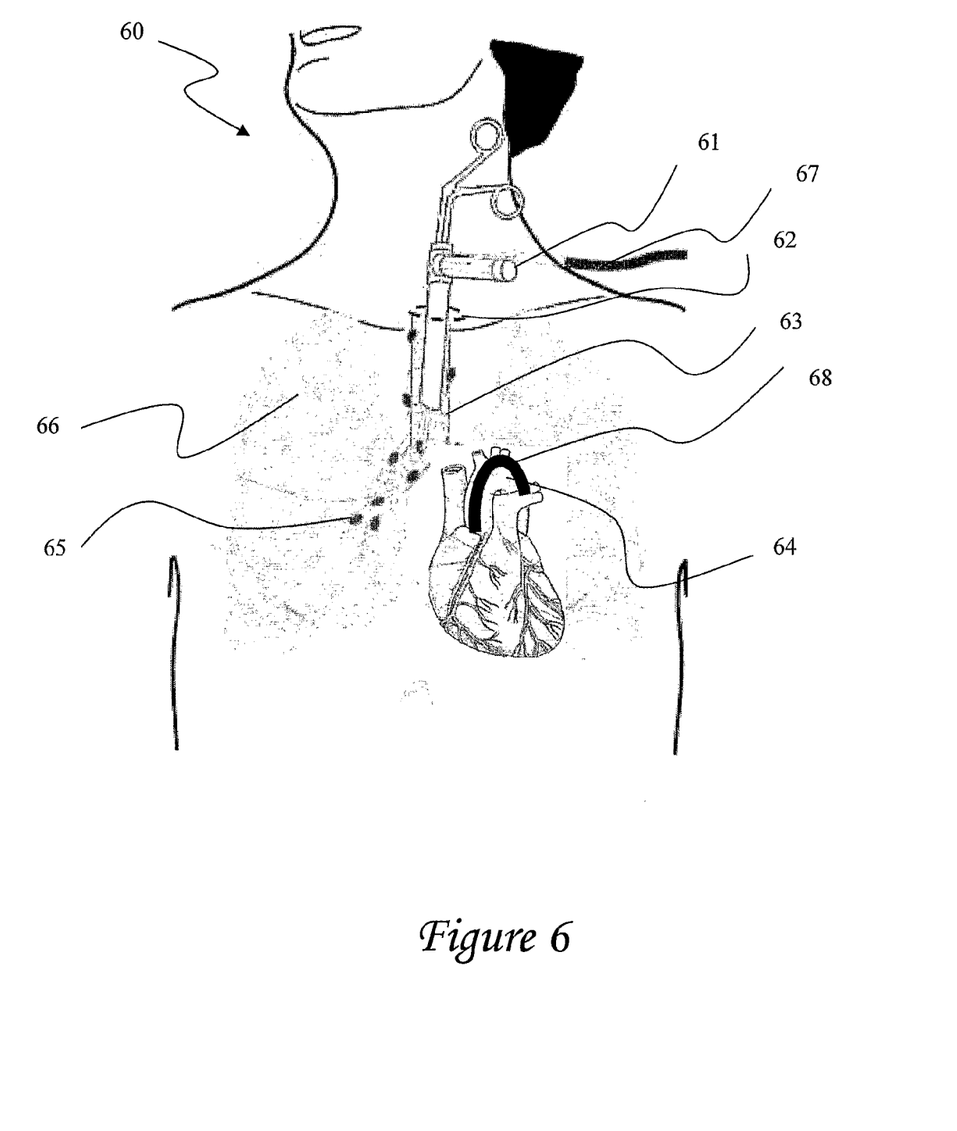
FIG. 6 schematically represents placement of the aortic pacemaker.

FIG. 6 schematically illustrates the procedure of cervical mediastinoscopy (60), a relatively simple procedure that may be performed in an outpatient's clinic and which is mainly used for biopsy of lymph nodes e.g. (65) in lung (66) cancer, but which also allows access to the aorta (64). A small incision is made in the supra-sternal notch (61), in which a mediastinoscope (62) is inserted (63). An optical fiber (67) may then be inserted to guide pacemaker electrode (68) implantation, the electrodes can then be fixed to aortic adventitia, possibly using an adaptor (not shown). Other methods of electrode implantation include canulation of the thoracic duct, the main lymphatic vessel which runs parallel and in proximity to the descending aorta, in the base of the neck aided by computer tomography (CT), ultrasound or endoscopic ultrasound guidance. Cardiac catheterization using arterial or venous access may also be used.

Figure 7:
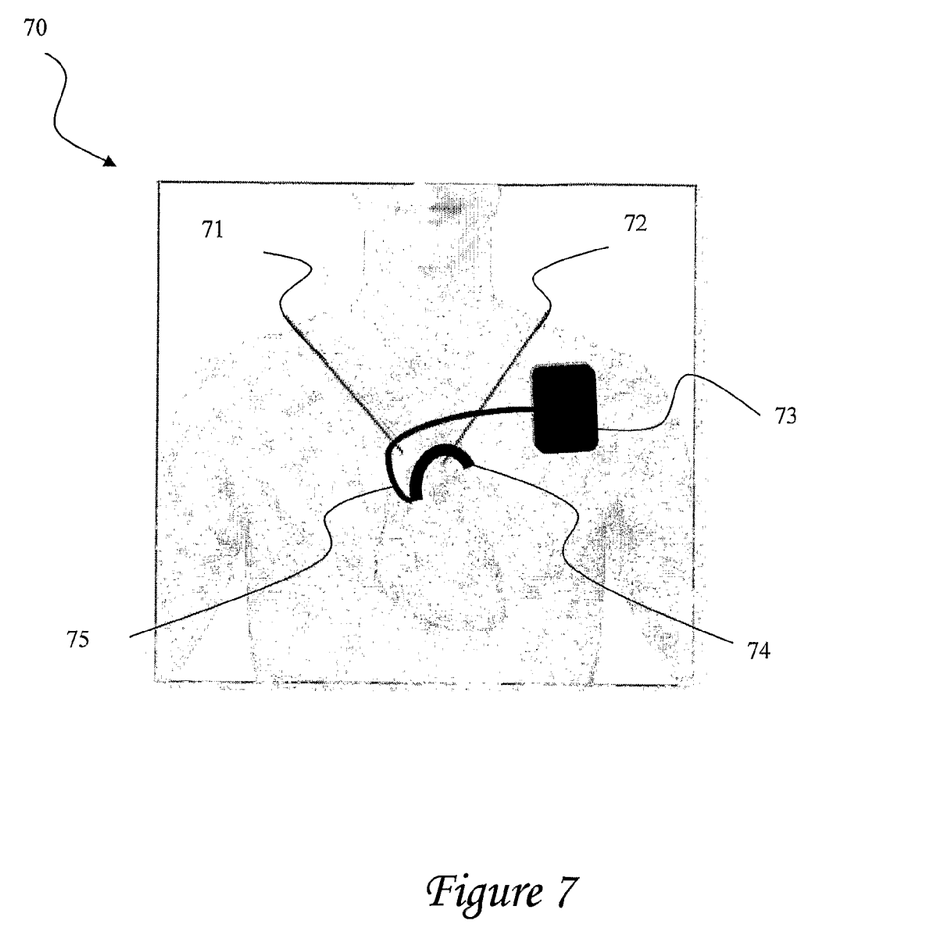
FIG. 7 schematically represents the components of the aortic pacemaker.

Reference is now made to FIG. 7, in which an implanted aortic pacemaker is shown (70). The electrode chain (74), which may optionally be with an adaptor and sensors, is implanted internally on the aorta (72). The electrode chain is then connected to the body of the pacemaker (73), which includes the processor or control unit, pulse generator and battery and which is preferably implanted in subcutaneous tissue, but may also be external.

Figure 8:
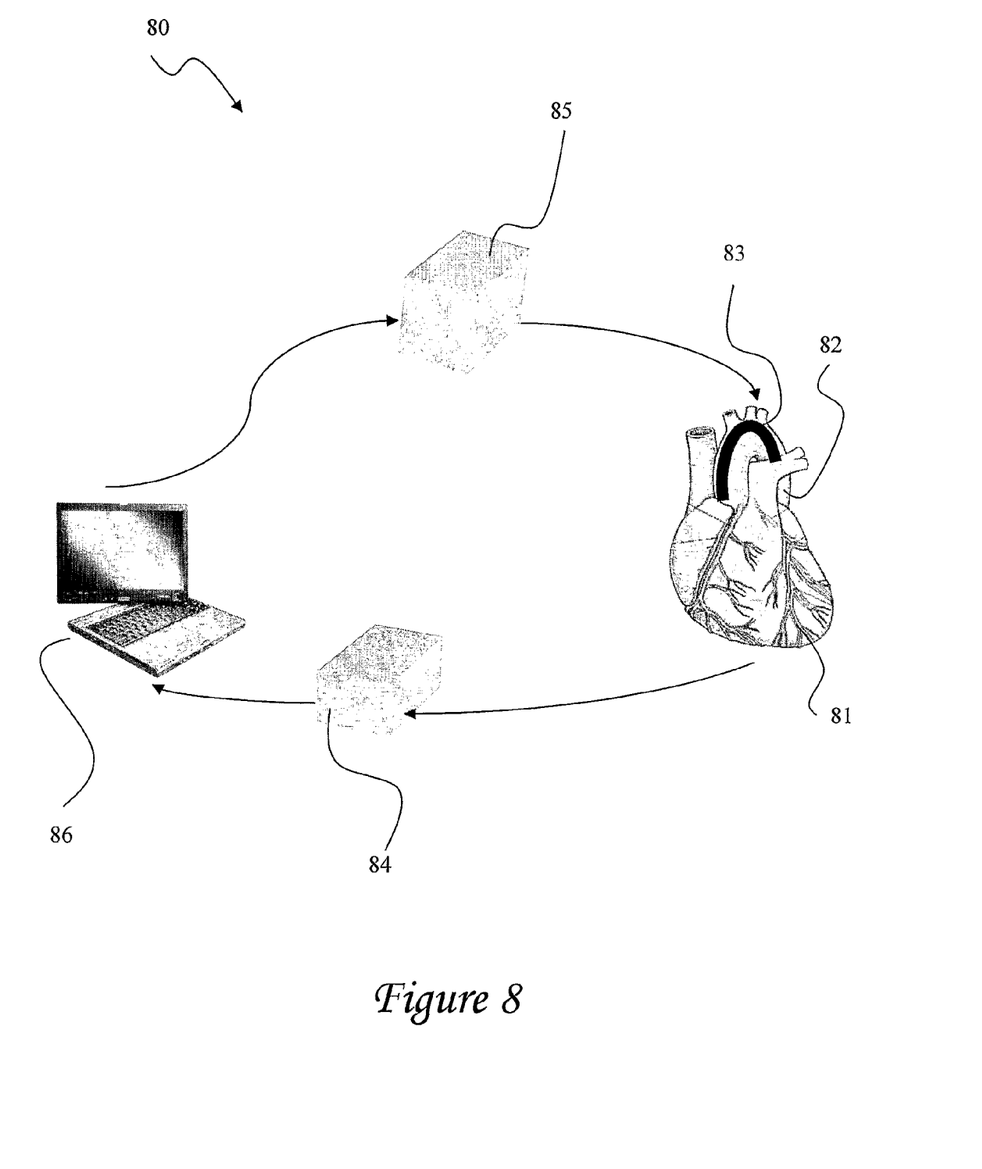
FIG. 8; schematically represents the method by which the aortic pacemaker operates.

Reference is now made to FIG. 8, which shows the method (80), by which the aortic pacemaker device works. A chain of electrodes (83) is implanted and attached to the aortic arch (82) of the heart (83), the electrode chain being the pacing means of the AAP. The electrode chain may be attached through an adaptor or may be attached directly to heart. Mechanical, chemical or electrical sensors may be placed directly on any location on the heart and may be disposed either externally or internally to the body. A sensing unit (84) obtains the data and a control unit (86), which may be part of the pacemaker body itself or in a remote location interprets and processes the data. The control unit then directs the pacemaker (85), also part of the pacemaker body, to pulse the aortic media through the electrode chain pacing means, triggering the appropriate feed-backed contraction waves in the aorta to improve cardiac and aortic function.

Figures 9A, 9B:
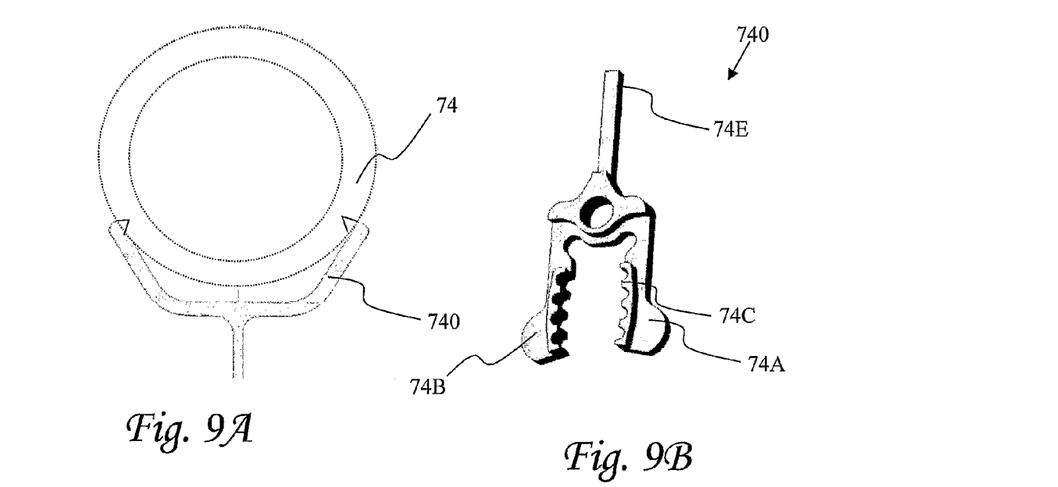
FIGS. 9A-9I schematically represent various possibly electrodes for use in this aortic pacemaker.
Figure 9C:
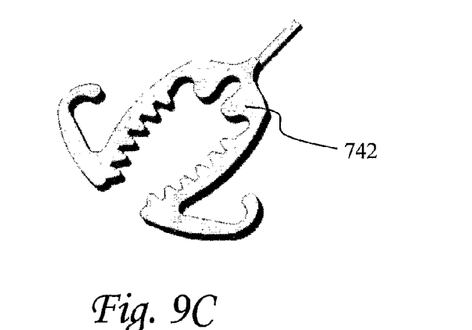
Figure 9D:
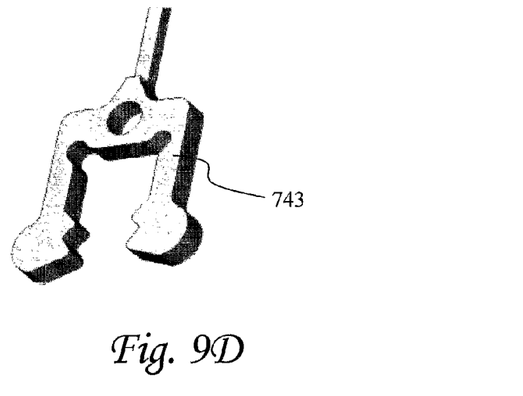
Figure 9E:
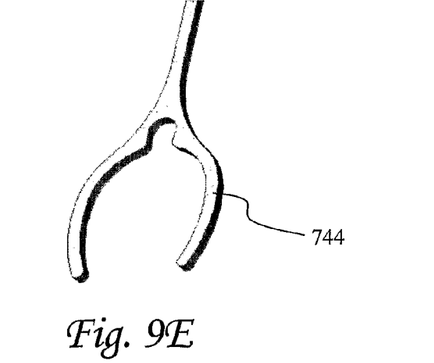
Figure 9F:
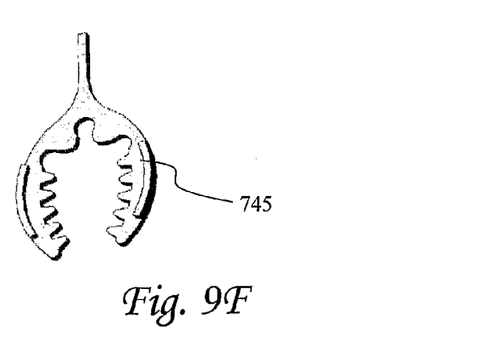
Figure 9G:
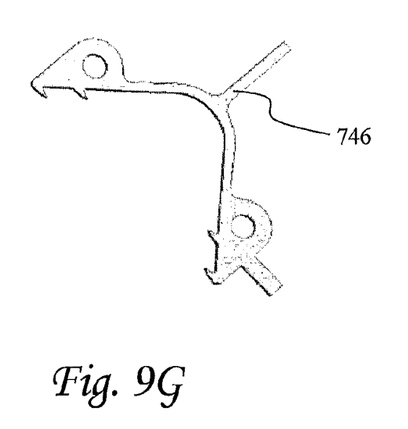
Figure 9H:
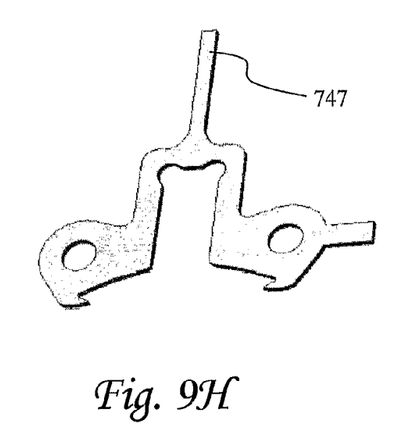
Figure 9I:
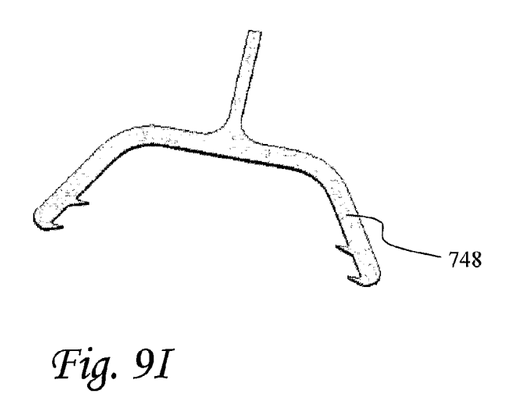

Lastly reference is now made to FIGS. 9A-9I, which shows out-of-scale illustrations of various electrodes of the aortic pacemaker according to few possible embodiments of the present invention. FIG. 9A shows a cross-section of an electrode (741) being temporarily or permanently, individually or as a part of an array of electrodes, clipped, clasped, immobilized, anchored, stitched, glued, incorporated or otherwise mounted on at least a portion of the aorta (74). The invention discloses an electrode for an AAP as defined in any of the above, comprising inter alia from members selected from a group of arms, anchoring means and electrical wiring. Hence for example, FIG. 9B shows a perspective view of an electrode (741), comprising in a non-limiting manner in a schematic non-in-scale manner multiple clamps (e.g., two clamps 74A, 74B). The electrode may further comprise of one or more handles (See arrows tip in 74A and 74B); fixating means, such as teeth etc (74c) and electrical wires (74E). Similarly, FIGS. 9C-9I shows possible electrodes 742-748, respectively.

The invention claimed is:
1. An implantable artificial pacemaker (AAP) comprising
   a. a plurality of sensors disposed internally or externally to the aorta, said electrodes forming an electrode chain, and adapted to identify at least one physiological parameter of the aorta;
   b. pacing means, adapted to create pulsating signals at a pre-selected frequency so as to provide a contraction wave in the aorta in response to said at least one physiological parameter;
said pacemaker is pacing the aorta so as to create a feed-backed contraction wave running along at least a portion of the aorta; and wherein said pulsating signals induce said contraction wave by electrical stimulation of muscle in said aorta, such that said pulsating signals created by said pacing means constrict the wall of at least a portion of the aorta.

2. The AAP according to claim 1, wherein said sensors are selected from a group consisting of chemical, mechanical or electrical sensors or any combination thereof.

3. The AAP according to claim 2, wherein said mechanical sensors detect parameters selected from a group consisting of aortic wall pressure, left ventricle end diastolic volume and pressure, end systolic volume and pressure, ventricular or atrial wall pressure, aortic wall potential, systolic and diastolic blood pressure or any combination thereof.

4. The AAP according to claim 2, wherein said chemical sensors detect parameters selected from a group consisting of pH in the myodcardium, lactate sensors, troponin sensors and any other chemical means to enable early detection of myodcardial ischemia.

5. The AAP according to claim 2, wherein said electrical sensors detect parameters selected from a group consisting of aortic diameter by M-mode echocardiography, aortic blood flow velocity by suing Doppler ultrasound, ECG, saturated hemoglobin fraction by using oximetry and input from any external device which is not part of the pacemaker by means of telemetry or any combination thereof.

6. The AAP according to claim 1, further comprising a processor capable of obtaining information from said sensors and triggering an appropriate contraction wave in the aortic media.

7. The AAP according to claim 6, wherein said processor is implantable as part of the pacemaker body; is external, able to transmit and receive information through telemetry; and any combination thereof.

8. The AAP according to claim 1, wherein said pacing means comprises a chain of monopolar or bipolar electrodes, placed along the aorta, in locations and distances according to the specific indication and hemodynamic needs.

9. The AAP according to claim 8, wherein said electrodes are an adjunct to the aorta either glued to the aorta or anchored to the aorta using immobilizing means.

10. The AAP according to claim 8, wherein said electrode chain is formed by using discrete electrodes or at least one adapter capable of accommodating a few electrodes and connecting them to the aorta.

11. The AAP according to claim 10, wherein said electrodes are connected to any location along the adapter.

12. The AAP according to claim 10 wherein said electrode anchoring means are separated by pre-determined distances.

13. The AAP according to claim 1 capable of modifications in its pulsating intensity, velocity or direction in response to feedback from the sensing means by pre-specified algorithms.

14. The AAP according to claim 1 adapted for driving blood anterogradely from the aorta to perfuse the body's end organs; retrogradely for increasing coronary artery blood flow or a combination of both; either simultaneous or sequential anterograde and retrograde contractions.

15. The AAP according to claim 1, said pulsating signals induce said contraction wave by electrical stimulation of muscle in said aorta without induction of increase in NO secretion on the wall of at least a portion of the aorta, such that said pulsating signals created by said pacing means constrict the wall of at least a portion of the aorta.

16. The method according to claim 1, wherein said pulsating signals inducing said contraction wave by electrical stimulation of muscle in said aorta without induction of increase in NO secretion on the wall of at least a portion of the aorta, such that said pulsating signals created by said pacing means constrict the wall of at least a portion of the aorta.

17. A method of managing aortic rhythm comprising:
a. implanting an AAP comprising:
   i. a plurality of sensors disposed internally or externally to the aorta, said electrodes forming an electrode chain, and adapted to identify at least one physiological parameter of the aorta;
   ii. pacing means, adapted to create pulsating signals at a pre-selected frequency so as to provide a contraction wave in the aorta in response to said at least one physiological parameter; and,
b. electrically stimulating at least a portion of the aorta by pulsating signals at said preselected frequency; thereby
c. inducing a feedbacked contraction wave running along at least a portion of the aorta;
wherein said pulsating signals inducing said contraction wave by electrical stimulation of muscle in said aorta, such that said pulsating signals created by said pacing means constrict the wall of at least a portion of the aorta.

18. The method according to claim 17, wherein said pulsating signals are provided by synchronizing and coordinating activation impulses in a portion of the aorta using electrical impulses.

19. The method according to claim 17 of augmenting cardiac output comprising synchronizing said pulsating aorta such that blood is pumped anterogradely.

20. The method according to claim 17 of increasing coronary perfusion comprising synchronizing said pulsating aorta such that blood is pumped retrogradely.

21. The method according to claim 17 of augmenting cardiac output while increasing coronary perfusion comprising synchronizing said pulsating aorta such that pulses originate in a certain point and proceed in both retrograde and anterograde directions.

22. The method according to claim 17, wherein said implanting is provided by a procedure selected from a group including applying minimally invasive cervical mediastinoscopy; applying canulation of the thoracic duct, applying cardiac catheterization using arterial or venous access; laparoscopy;
open surgery, or any combination thereof.

23. The method according to claim 17, comprising activating contraction waves in the aortic media at a rate of 1 in every N heartbeats, where N is any integer equal to or greater than 1, but preferably N is between 1 and 6.

24. The method according to claim 17, comprising self-adjusting velocity of said contraction wave according to aortic smooth muscle depolarization and repolarization rates so as to avoid aortic contraction during systole.

25. The method according to claim 17, comprising stimulating of the contraction wave area, duration or intensity so as to promote aortic muscular layer adaptation to rhythmical contraction or for inducing aortic muscle hypertrophy or hyperplasia.

26. The method according to claim 17, especially adapted for inducing smooth muscle proliferation and improving aortic contraction performance over time, comprising implanting an AAP comprising oscillatory means; pulsating signals at a preselected frequency, and hence stimulating the aorta.

27. The method according to claim 17, especially adapted for treating acute cardiac insult selected from a group including cardiogenic shock; myocardial infarction or myocarditis, comprising the steps of implanting an AAP following said insult, pulsating signals at a preselected frequency, and hence stimulating the aorta.

28. The method according to claim 17, especially adapted for treating medical conditions selected from a group including congestive heart failure, pulmonary edema, aortic regurgitation and aortic aneurysm comprising the steps of implanting an AAP, continuously pulsating signals at a preselected frequency, hence stimulating the aorta and maintaining hemodynamic equilibrium.

29. The method according to claim 17, especially adapted for treating exertional angina, comprising the steps of implanting an AAP, triggering AAP activation in times of need, pulsating signals at a preselected frequency, hence stimulating the aorta.

30. The method according to claim 29, wherein said triggering is provided by means selected from a group including sensors, manual activation by a patient, manual activation by a medical care-giver, manual activation from a remote site especially an emergency hot line, and any combination thereof.

31. The method according to claim 30, wherein said pulsating is activated by a group of triggers including intrinsic cardiac activity, artificial cardiac pacemaker or hemodynamics sensed by the aortic electrodes.

* * * * *